US00PP09004P

United States Patent [19]

Stravers

[11] Patent Number: Plant 9,004

[45] Date of Patent: Dec. 6, 1994

[54] *GERBERA JAMESONII* PLANT NAMED TEROZET

[75] Inventor: Lambertus J. M. Stravers, Kudelstaart, Netherlands

[73] Assignee: Terra Nigra B.V., De Kwakel, Netherlands

[21] Appl. No.: 172,263

[22] Filed: Dec. 23, 1993

[51] Int. Cl.[5] ..... A01H 5/00
[52] U.S. Cl. ..... Plt./68.1
[58] Field of Search ..... Plt. 68.1

*Primary Examiner*—James R. Feyrer

[57] ABSTRACT

A new and distinct cultivar of Gerbera plant named 'Terozet' as illustrated and described, characterized by its single type, and ray florets with a distinct salmon color with a pink blush, lighter margins and tips, a very distinctive green-black disc floret, the outermost florets of which display white stigmas and the middle flowers of which show yellow anthers, pink perianth lobe color and 120 mm overall flower diameter.

1 Drawing Sheet

BACKGROUND OF THE INVENTION

The present invention comprises a new and distinct cultivar of *Gerbera jamesonii*, referred to by the cultivar name 'Terozet'. 'Terozet' was originated from a hybridization program in De Kwakel, The Netherlands in 1990. The female parent was '83.242', and the male parent was 'C.P.6'. The female parent '83.242' differs from 'Terozet' by its sharp yellow color and dark black disc floret, its low productivity, its smaller flower diameter (approx. 100 mm) and its good vase-life. '83.242' has not been patented in the United States. Moreover, it has been available to others outside the company. The male parent 'C.P.6' differs from 'Terozet' by its different pink color, its high productivity, and its shorter stems. 'C.P.6' has not been patented in the United States. It was not available to others outside the company. The new cultivar was selected by me from the progeny of the stated parentage on or about November 1990. The first asexual reproduction of 'Terozet' was accomplished when vegetative cuttings for tissue culture initiation were taken on November 1990 in De Kwakel, The Netherlands. The new cultivar is presently being propagated by cuttings and tissue culture. Horticultural examination of selected units initiated November 1990 has demonstrated that the combination of characteristics as herein disclosed for 'Terozet' are firmly fixed and are retained through successive generations of asexual reproduction.

The following observations, measurements and comparisons describe plants grown in De Kwakel, The Netherlands, under greenhouse conditions which closely approximate those generally used in commercial practice. The following traits have been repeatedly observed and are determined to be basic characteristics of 'Terozet', which in combination distinguish this Gerbera from its parents and all other varieties of which I am aware:

1. Type: Single.
2. Color of ray floret: Distinctive predominantly orange color, with a pink blush fused over the basal and central areas of the laminas, becoming progressively less intensely pink and more yellow toward the margin and apex.
3. Color of disc floret: Green-black.
4. Color of perianthy lobe: Orange with a light pink blush which is heavier in the central and basal portions.

5. Diameter of flower head: Large 120 mm.

Of the many commercial cultivars known to me, there is no cultivar similar in comparision to 'Terozet'.

BRIEF DESCRIPTION OF THE FIGURE OF THE DRAWING

The accompanying photographic drawing shows typical inflorescence characteristics nearly true as possible. In the following description, color references are made to The Royal Horticultural Society Color Chart (RHS). The color values were determined at approximately 14:00 p.m. on Sep. 11, 1993 under natural light at De Kwakel.

BOTANICAL DESCRIPTION OF THE PLANT

Botanical: *Gerbera jamesonii* cv 'Terozet'.

INFLORESCENCE

A. Capitulum:
- *Form.*—Flat shaped.
- *Type.*—Single.
- *Diameter across face.*—120 mm.

B. Corolla of ray florets:
- *Color (general tonality from a distance of* 3 *meters)*.—Pink.
- *Color (topside)*.—Yellow (RHS 29B,C+9D).
- *Color (bottom)*.—Yellow (RHS 2C).

C. Corolla of disc florets:
- *Color (mature)*.—Green purple (RHS 145B+185A).
- *Color (immature)*.—Purple (RHS 187A).

D. Reproductive organs:
- *Stigma.*—White (RHS 155C).
- *Anthers.*—Yellow (RHS 6B).
- *Pappus.*—Yellow (RHS 34D).

PLANT

A. General appearance:
- *Flowering season in greenhouse.*—Year round, with less productivity during the winter period due to changing light intensity.
- *Productivity in soil.*—27 flowers per plant, per year.
- *Productivity in rockwool.*—40 flowers per plant, per year.
- *Height.*—40 cm.

B. Foliage:
- *Color (abaxial)*.—Green RHS 139A.

*Color (adaxial).*—Green RHS 139A.

*Shape.*—The angle of apex: Right angle. The shape of apex: Rounded. The margin of lobes: Irregular.

C. Disease resistance: No special disease resistance.

OTHER CHARACTERISTICS

The following traits have been repeatedly observed and are determined to be basic characteristics of 'Terozet', which in combination distinguish this Gerbera as a new and distinct cultivar.

Leaf blade:

*Length.*—Approximately 30 cm (without petiole).

*Width.*—Approximately 22 cm.

*Thickness.*—Medium.

*Blistering.*—Medium.

*Pubescence.*—On upper side (midrib excluded): Medium.

*Depth of cuts or incisions in leaf.*—Basal part: Deep. Central part: Deep. Distal part: Shallow.

*Color.*—Upper side of the leaf blade is green (RHS 139A).

*Glossiness on upper side.*—Medium.

*Angle of apex.*—Right angle.

*Shape of apex.*—Rounded.

*Margin of lobes.*—Irregular.

*Extensions of margin.*—Medium.

*Petiole length.*—Long; 15 cm.

*Petiole anthocyanin coloration.*—Medium.

Peduncle:

*Length.*—Long (approx. 76–80 cm).

*Cross section.*—Elliptic.

*Tendency to fasciation.*—Present.

*Thickness.*—Medium.

*Strength.*—Medium.

*Pubescence.*—Medium.

*Color.*—Medium green.

*Anthocyanin coloration.*—At base: Medium. At top: Absent.

*Involucral bracts.*—Absent.

Flower head:

*Type.*—Single.

*Diameter.*—Large (approx. 120 mm).

*Involucre.*—Height: Medium (20 mm). Diameter: Medium (45 mm). Number of bracts: Medium (approx. 55). Longitudinal axis of bracts of inner rows: Straight. Anthocyanin: Absent. Pubescence: Medium.

*Ray florets.*—Number: Medium (approx. 55). Shape: Elliptic. Longitudinal axis outer row: Reflexing. Longitudinal axis inner row: Straight.

*Outer ray florets.*—Cross section: Flat. Length: Medium (60 mm). Width: Medium. Longitudinal folding: Medium. Angle of apex: Right angle. Shape of apex: Pointed. Incisions of apex: Present. Number: two. Depth: shallow. Length of free petals: Short. Color distribution on inner side: Uniform. Edge of different color: Absent. Striation: Absent. Claw spot: Present.

Disc florets:

*Diameter of disc.*—Medium (approx. 45 mm).

*Main color perianth lobes.*—Female flowers: pink (RHS 38A). Male flowers: pink (RHS 38A).

Reproductive parts:

*Stigma.*—Main color white (RHS 155C).

*Anthers.*—Main color yellow (RHS 6B).

*Pappus.*—Main color yellow (RHS 34D).

*Fertility.*—Fertility as well as the seedsetting are very good.

I claim:

1. A new and distinct cultivar of Gerbera plant named 'Terozet' as illustrated and described, characterized by its single type, ray florets with a distinct salmon color which have a pink blush and lighter margins, a very distinctive green-black disc floret, the outermost florets of which display white stigmas and the middle flowers of which show yellow anthers, pink perianth lobe color and 120 mm overall flower diameter.

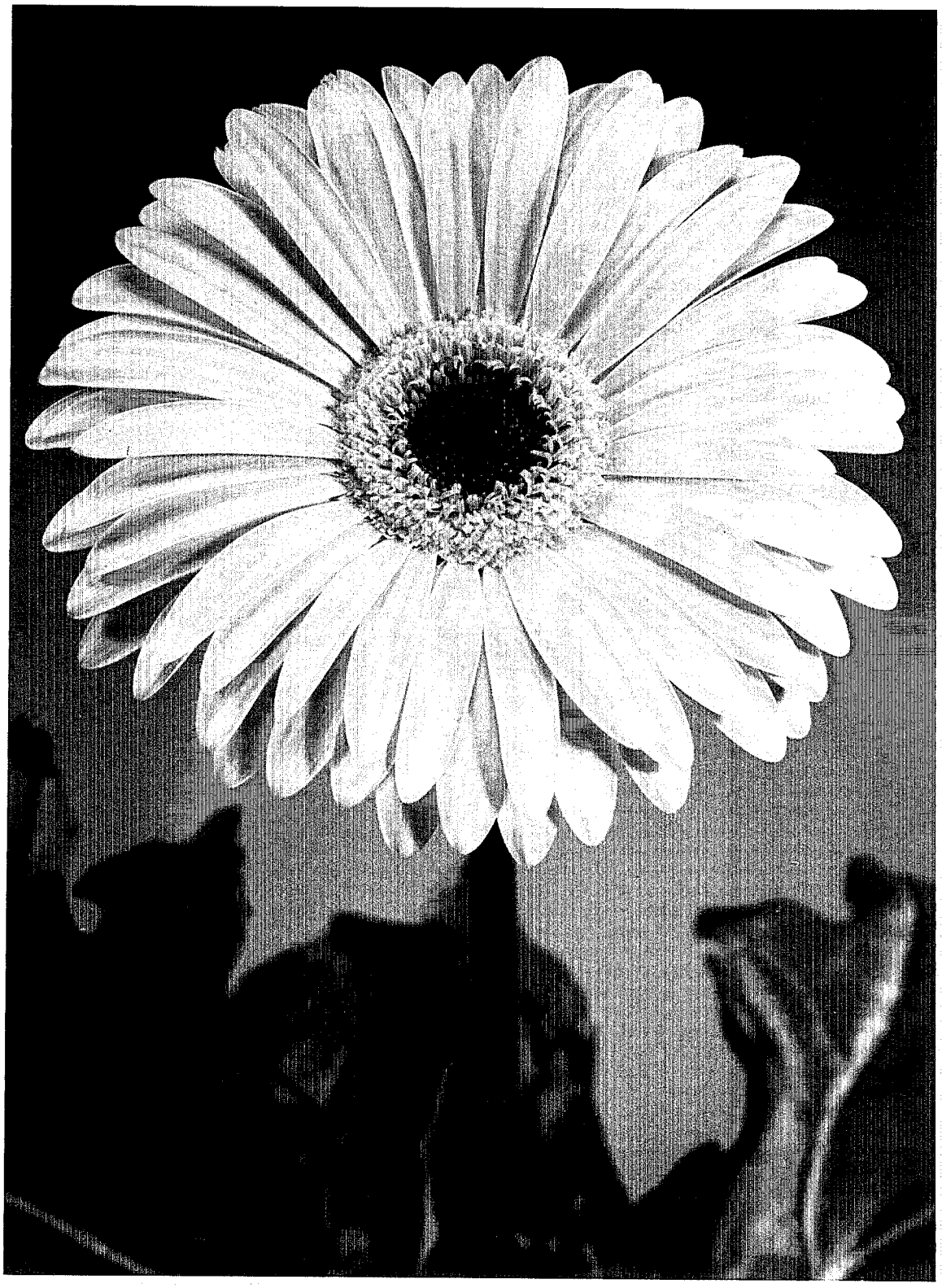

* * * * *